US009808012B2

(12) United States Patent
Ji et al.

(10) Patent No.: US 9,808,012 B2
(45) Date of Patent: Nov. 7, 2017

(54) BIOCIDAL COMPOSITION

(75) Inventors: Kathy Jing Ji, Shanghai (CN); Zheng Q. Wen, Shanghai (CN)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 1018 days.

(21) Appl. No.: 13/816,697

(22) PCT Filed: Aug. 13, 2010

(86) PCT No.: PCT/CN2010/075974
§ 371 (c)(1),
(2), (4) Date: Oct. 6, 2014

(87) PCT Pub. No.: WO2012/019360
PCT Pub. Date: Feb. 16, 2012

(65) Prior Publication Data
US 2015/0018317 A1   Jan. 15, 2015

(51) Int. Cl.
| | | |
|---|---|---|
| *A01N 57/20* | (2006.01) | |
| *C09K 8/68* | (2006.01) | |
| *C09K 8/18* | (2006.01) | |
| *A01N 57/34* | (2006.01) | |
| *C09D 5/14* | (2006.01) | |
| *C02F 1/50* | (2006.01) | |

(52) U.S. Cl.
CPC .............. *A01N 57/20* (2013.01); *A01N 57/34* (2013.01); *C09D 5/14* (2013.01); *C09K 8/18* (2013.01); *C09K 8/68* (2013.01); *C02F 1/50* (2013.01); *C02F 2303/08* (2013.01)

(58) Field of Classification Search
None
See application file for complete search history.

(56) References Cited

U.S. PATENT DOCUMENTS 5,063,213 A * 11/1991 Whitekettle ........... A01N 57/34
162/161
6,214,777 B1    4/2001 Li et al.
7,618,055 B2   11/2009 Chuah et al.

\* cited by examiner

*Primary Examiner* — Kortney L. Klinkel
*Assistant Examiner* — William Lee
(74) *Attorney, Agent, or Firm* — Tifani M. Edwards

(57) ABSTRACT

A biocidal composition comprising tributyl tetradecyl phosphonium chloride and tetrakis(hydroxymethyl)phosphonium sulfate at a weight ratio of 2:1 to 1:10, and its use for the control of microorganisms in aqueous and water-containing systems.

3 Claims, No Drawings

BIOCIDAL COMPOSITION

FIELD OF THE INVENTION

The invention relates to a biocidal composition and methods of its use for the control of microorganisms in aqueous and water-containing systems. The composition comprises tributyl tetradecyl phosphonium chloride and tetrakis(hydroxymethyl)phosphonium sulfate.

BACKGROUND OF THE INVENTION

Water systems provide fertile breeding grounds for algae, bacteria, viruses, and fungi some of which can be pathogenic. Such microorganism contamination can create a variety of problems, including aesthetic unpleasantries such as slimy green water, serious health risks such as fungal, bacterial, or viral infections, and mechanical problems including plugging, corrosion of equipment, and reduction of heat transfer.

Biocides are commonly used to disinfect and control the growth of microorganisms in aqueous and water containing systems. However, not all biocides are effective against a wide range of microorganisms and/or temperatures, and some are incompatible with other chemical treatment additives. In addition, some biocides do not provide microbial control over long enough time periods.

While some of these shortcomings can be overcome through use of larger amounts of the biocide, this option creates its own problems, including increased cost, increased waste, and increased likelihood that the biocide will interfere with the desirable properties of the treated medium. In addition, even with use of larger amounts of the biocide, many commercial biocidal compounds cannot provide effective control due to weak activity against certain types of microorganisms or resistance of the microorganisms to those compounds.

It would be a significant advance in the art to provide biocide compositions for treatment of water systems that provide one or more of the following advantages: increased efficacy at lower concentrations, compatibility with physical conditions and other additives in the treated medium, effectiveness against a broad spectrum of microorganisms, and/or ability to provide both short term and long term control of microorganisms.

BRIEF SUMMARY OF THE INVENTION

In one aspect, the invention provides a biocidal composition. The composition comprises: tributyl tetradecyl phosphonium chloride and tetrakis(hydroxymethyl)-phosphonium sulfate at a weight ratio of the tributyl tetradecyl phosphonium chloride to the tetrakis(hydroxymethyl)phosphonium sulfate of 2:1 to 1:10.

In a second aspect, the invention provides a method for controlling microorganisms in aqueous or water containing systems. The method comprises treating the system with an effective amount of a biocidal composition as described herein.

DETAILED DESCRIPTION OF THE INVENTION

As noted above, the invention provides a biocidal composition and methods of using it in the control of microorganisms. The composition comprises: tributyl tetradecyl phosphonium chloride and tetrakis(hydroxymethyl)phosphonium sulfate. It has surprisingly been discovered that combinations of tributyl tetradecyl phosphonium chloride and tetrakis(hydroxymethyl)phosphonium sulfate at the weight ratios described herein are synergistic when used for microorganism control in aqueous or water containing media. That is, the combined materials result in improved biocidal properties than would otherwise be expected based on their individual performance. The synergy permits reduced amounts of the materials to be used to achieve the desired biocidal performance, thus reducing problems caused by growth of microorganisms in industrial process waters while potentially reducing environmental impact and materials cost.

For the purposes of this specification, the meaning of "microorganism" includes, but is not limited to, bacteria, fungi, algae, and viruses. The words "control" and "controlling" should be broadly construed to include within their meaning, and without being limited thereto, inhibiting the growth or propagation of microorganisms, killing microorganisms, disinfection, and/or preservation. In some preferred embodiments, "control" and "controlling" mean inhibiting the growth or propagation of microorganisms. In further embodiments, "control" and "controlling" mean the killing of microorganisms.

In some embodiments of the invention, the weight ratio of the tributyl tetradecyl phosphonium chloride to the tetrakis(hydroxymethyl)phosphonium sulfate is between about 2:1 and 1:6, or alternatively 2:1 and 1:4, or alternatively 2:1 and 1:2. In some embodiments, the weight ratio is 2:1, alternatively 1:1, or alternatively 1:2.

The composition of the invention is useful for controlling microorganisms in a variety of aqueous and water containing systems. Examples of such systems include, but are not limited to, paints and coatings, aqueous emulsions, latexes, adhesives, inks, pigment dispersions, household and industrial cleaners, detergents, dish detergents, mineral slurries polymer emulsions, caulks and adhesives, tape joint compounds, disinfectants, sanitizers, metalworking fluids, construction products, personal care products, textile fluids such as spin finishes, industrial process water (e.g. oilfield water, pulp and paper water, cooling water), oilfield functional fluids such as drilling muds and fracturing fluids, fuels, air washers, wastewater, ballast water and filtration systems. Preferred aqueous systems are metal working fluids, household and industrial cleaners, industrial process water, oilfield functional fluids, wastewater and paints and coatings. Particularly preferred are industrial process water, oilfield functional fluids, wastewater and textile fluids such as spin finishes.

Further preferred, the composition may be used in oil and gas field injection, produced fluids, fracturing fluids and functional fluids, oil and gas wells, oil and gas operation, separation, storage, and transportation systems, oil and gas pipelines, oil and gas vessels, and fuel. The composition is especially useful in aqueous fluids added to or produced by oil and gas well.

A person of ordinary skill in the art can readily determine, without undue experimentation, the effective amount of the composition that should be used in any particular application to provide microorganism control. By way of illustration, a suitable concentration is 10 ppm to 5,000 ppm active ingredient ((total for both tributyl tetradecyl phosphonium chloride and tetrakis(hydroxymethyl)phosphonium sulfate). In some embodiments of the invention, the active ingredients of the composition (total for both tributyl tetradecyl phosphonium chloride and tetrakis(hydroxymethyl)phosphonium sulfate) are present in an amount of at least 10 ppm and up to 5,000 ppm. In some embodiments of the invention, the active ingredients of the composition are present in an amount of at least 20 ppm, alternatively at least 50 ppm, alternatively at least 100 ppm, alternatively at least 150 ppm, alternatively at least 200 ppm. In some embodiments, the active ingredients of the composition are present in an amount of no more than 2,000 ppm, alternatively no more than 1,000 ppm, alternatively no more than 500 ppm, alternatively no more than 400 ppm, alternatively no more than 300 ppm, alternatively no more than 250 ppm, alternatively no more than 200 ppm, alternatively no more than 100 ppm, alternatively no more than 50 ppm. Concentrations mentioned above are based on the total weight of the aqueous or water containing system including the active ingredients.

The components of the composition may be added to the aqueous or water containing system separately, or pre-blended prior to addition. A person of ordinary skill in the art can easily determine the appropriate method of addition. The composition may be used in the system with other additives such as, but not limited to, surfactants, ionic/nonionic polymers and scale and corrosion inhibitors, oxygen scavengers, and/or additional biocides.

The following examples are illustrative of the invention but are not intended to limit its scope. Unless otherwise indicated, the ratios, percentages, parts, and the like used herein are by weight.

EXAMPLES

Example 1 Synergistic Effect of TTPC and THPS Against Microorganisms

In this example, tributyl tetradecyl phosphonium chloride (TTPC), tetrakis(hydroxymethyl)phosphonium sulfate (THPS), and combinations of TTPC and THPS are tested at different concentrations for efficacy against bacteria isolated from a industrial cooling water sample. Water samples containing a final bacterial concentration of about $5 \times 10^7$ CFU/ml are used. Biocide solutions are prepared and diluted in sterile deionized water and used within 2 hours.

Time-kill tests are carried out to determine the threshold concentrations required for biocide activity in the cooling water samples. Tests are conducted in a 96-deep well block format using a total sample volume of 600 µl for all evaluations. In these samples, no more than 10% of the total volume consists of the biocide and organism solution and all non-matrix additions are normalized for all samples. Each experimental 96-well block contains biocide-treated samples and control samples which lack biocide. The biocides are added to the bacterial suspension at various concentrations and mixed well. The mixture samples are then incubated at 37° C. At several time intervals starting from 1 hour, viable bacteria left in the mixture are determined using the MPN method of serial dilution.

Synergy Index (SI) is calculated as shown below. An SI value of less than 1 indicates synergy.

$$SI = Ca/CA + Cb/CB$$

Where:
Ca: Concentration of biocide A required to achieve bacterial concentrations of $2 \times 10^3$ CFU/ml or less when used in combination CA: Concentration of biocide A required to achieve bacterial concentrations of $2 \times 10^3$ CFU/ml or less when used alone Cb: Concentration of biocide B required to achieve bacterial concentrations of $2 \times 10^3$ CFU/ml or less when used in combination CB: Concentration of biocide B required to achieve bacterial concentrations of $2 \times 10^3$ CFU/ml or less when used alone Table 1 summarizes the concentrations of TTPC, THPS, and combinations thereof needed to achieve bacterial concentrations of $2 \times 10^3$ CFU/ml or less in the cooling water sample.

TABLE 1

| Concentration of active (ppm) | 4 hr | 24 hr | 48 hr | 3 day | 5 day | 7 day |
|---|---|---|---|---|---|---|
| TTPC alone | 30 | 40 | 40 | 40 | 40 | 40 |
| THPS alone | 100 | 75 | 75 | 75 | 75 | 75 |
| TTPC in combo | 5 | 5 | 5 | 5 | 5 | 5 |
| THPS in combo |  | 50 |  |  |  |  |
| SI |  | 0.79 |  |  |  |  |
| TTPC:THPS Ratio |  | 1:10 |  |  |  |  |
| TTPC in combo | 10 | 10 | 10 | 10 | 10 | 10 |
| THPS in combo | 20 | 20 | 40 | 40 | 40 | 40 |
| SI | 0.53 | 0.52 | 0.78 | 0.78 | 0.78 | 0.78 |
| TTPC:THPS Ratio | 1:2 | 1:2 | 1:4 | 1:4 | 1:4 | 1:4 |
| TTPC in combo | 20 | 20 | 20 | 20 | 20 | 20 |
| THPS in combo | 10 | 20 | 30 | 30 | 30 | 30 |
| SI | 0.77 | 0.77 | 0.90 | 0.90 | 0.90 | 0.90 |
| TTPC:THPS Ratio | 2:1 | 1:1 | 1:1.5 | 1:1.5 | 1:1.5 | 1:1.5 |

The data in Table 1 demonstrates that synergy is observed over a ratio range of TTPC to THPS of 2:1 to 1:10.

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

The invention claimed is:

1. A biocidal composition comprising: tributyl tetradecyl phosphonium chloride and tetrakis(hydroxymethyl)phosphonium sulfate at a weight ratio of 1:1 to 1:10.

2. A method for controlling microorganism growth in an aqueous or water-containing system, the method comprising treating the aqueous or water-containing system with an effective amount of a composition according to claim 1.

3. A method according to claim 2 wherein the aqueous or water-containing system is paint, coating, aqueous emulsion, latex, adhesive, ink, pigment dispersion, household or industrial cleaner, detergent, dish detergent, mineral slurry polymer emulsion, caulk, adhesive, tape joint compound, disinfectant, sanitizer, metalworking fluid, construction product, personal care product, textile fluid, spin finish, industrial process water, oilfield functional fluid, fuel, air washer, wastewater, ballast water or filtration system.

* * * * *